(12) United States Patent
Hayter et al.

(10) Patent No.: US 11,116,898 B2
(45) Date of Patent: Sep. 14, 2021

(54) ARTIFICIAL PANCREAS INTEGRATED CGM ARCHITECTURES AND DESIGNS

(71) Applicant: Abbott Diabetes Care Inc., Alameda, CA (US)

(72) Inventors: Gary Alan Hayter, Oakland, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 260 days.

(21) Appl. No.: 16/017,584

(22) Filed: Jun. 25, 2018

(65) Prior Publication Data

US 2018/0369479 A1   Dec. 27, 2018

Related U.S. Application Data

(60) Provisional application No. 62/525,164, filed on Jun. 26, 2017.

(51) Int. Cl.
*A61M 5/172* (2006.01)
*G16H 40/63* (2018.01)
(Continued)

(52) U.S. Cl.
CPC .......... *A61M 5/1723* (2013.01); *G16H 20/17* (2018.01); *G16H 40/63* (2018.01); *G16H 50/20* (2018.01); *G16H 50/70* (2018.01); *A61M 5/14244* (2013.01); *A61M 2005/14208* (2013.01); *A61M 2205/3303* (2013.01); (Continued)

(58) Field of Classification Search
CPC ............ A61M 5/1723; A61M 5/14244; A61M 2205/3303; A61M 2205/3561; A61M 2205/3584; A61M 2205/50; A61M 2205/502; A61M 2205/52; G16H 20/17
See application file for complete search history.

(56) References Cited

U.S. PATENT DOCUMENTS 4,392,849 A   7/1983   Petre et al.
5,733,259 A   3/1998   Valcke et al.
(Continued)

OTHER PUBLICATIONS

PCT Application No. PCT/2018/039330, International Search Report and Written Opinion of the International Searching Authority dated Sep. 17, 2018.

*Primary Examiner* — Nathan R Price
*Assistant Examiner* — Justin L Zamory
(74) *Attorney, Agent, or Firm* — Baker Botts L.L.P.

(57) ABSTRACT

A system for managing a patient's glucose level includes a glucose sensor to generate and store data signals for measurements of the patient's glucose level made by the glucose sensor; an insulin pump; and sensor electronics operatively coupled to the glucose sensor, the sensor electronics comprising a memory storing one or more predetermined characteristics associated with the sensor electronics; and a computing device in electronic communication with the sensor electronics. The computing device comprises a processor configured to operate the sensor electronics to (i) receive the generated data signals, (ii) obtain the one or more predetermined sensor characteristics from the memory and (iii) execute a closed-loop algorithm to provide insulin delivery instructions to an insulin pump by at least using the data signals and predetermined characteristics.

24 Claims, 4 Drawing Sheets

(51) Int. Cl.
  *G16H 50/20* (2018.01)
  *G16H 50/70* (2018.01)
  *G16H 20/17* (2018.01)
  *A61M 5/142* (2006.01)

(52) U.S. Cl.
  CPC ............. *A61M 2205/3561* (2013.01); *A61M 2205/3584* (2013.01); *A61M 2205/50* (2013.01); *A61M 2205/502* (2013.01); *A61M 2205/52* (2013.01); *A61M 2230/201* (2013.01)

(56) References Cited

U.S. PATENT DOCUMENTS

| | | | | |
|---|---|---|---|---|
| 6,558,351 | B1* | 5/2003 | Steil | A61B 5/6849 604/131 |
| 7,404,796 | B2* | 7/2008 | Ginsberg | A61P 3/10 600/365 |
| 2003/0060753 | A1 | 3/2003 | Starkweather et al. | |
| 2003/0130616 | A1 | 7/2003 | Steil et al. | |
| 2003/0212317 | A1 | 11/2003 | Kovatchev et al. | |
| 2004/0122353 | A1* | 6/2004 | Shahmirian | A61M 5/1723 604/65 |
| 2004/0147872 | A1 | 7/2004 | Thompson | |
| 2005/0192557 | A1 | 9/2005 | Brauker et al. | |
| 2006/0173406 | A1 | 8/2006 | Hayes et al. | |
| 2006/0189863 | A1 | 8/2006 | Peyser et al. | |
| 2008/0021436 | A1 | 1/2008 | Wolpert et al. | |
| 2009/0005665 | A1 | 1/2009 | Hayter et al. | |
| 2009/0012376 | A1 | 1/2009 | Agus | |
| 2009/0105636 | A1 | 4/2009 | Hayter et al. | |
| 2009/0312622 | A1 | 12/2009 | Regittnig | |
| 2010/0057040 | A1 | 3/2010 | Hayter | |
| 2010/0057041 | A1 | 3/2010 | Hayter | |
| 2010/0057042 | A1 | 3/2010 | Hayter | |
| 2010/0057057 | A1 | 3/2010 | Hayter et al. | |
| 2012/0318670 | A1 | 12/2012 | Karinka et al. | |
| 2016/0302701 | A1* | 10/2016 | Bhavaraju | A61B 5/1495 |

* cited by examiner

ARTIFICIAL PANCREAS INTEGRATED CGM ARCHITECTURES AND DESIGNS

RELATED APPLICATION

The present application claims priority under 35 U.S.C. § 119(e) to U.S. Provisional Application No. 62/525,164 filed Jun. 26, 2017, entitled "Artificial Pancreas Integrated CGM Architectures and Designs," the disclosure of which is incorporated herein by reference for all purposes.

BACKGROUND

The present invention relates to continuous glucose monitoring (CGM) systems or flash glucose monitoring with insulin therapy. More specifically, the present invention relates to a continuous glucose monitoring system including computing devices to utilize detected analyte levels and stored sensor information for monitoring, diagnosis and analysis.

The technical advancements and commercial adoption of smartphones and cloud-based computing has facilitated the development of glucose monitoring systems and methods, for example by promoting standardized communication technologies such as Bluetooth® and the World-Wide-Web.

SUMMARY

An environment for realizing artificial pancreas systems that utilize communication technologies and other technologies is described. Systems, devices, and methods for integrating continuous glucose monitoring (CGM) or flash glucose monitoring with insulin therapy are provided. One or more embodiments of the present invention include a system for managing a patient's glucose level including an analyte sensor to generate and store data signals for measurements of the patient's glucose level made by the analyte sensor; an insulin pump; and sensor electronics operatively coupled to the analyte sensor. The sensor electronics comprise a memory storing one or more predetermined characteristics associated with the sensor electronics. The system further includes a computing device in electronic communication with the sensor electronics, the computing device comprising a processor configured to operate the sensor electronics to (i) receive the generated data signals, (ii) obtain the one or more predetermined sensor characteristics from the memory and (iii) execute a closed-loop algorithm to provide insulin delivery instructions to an insulin pump by at least using the data signals and predetermined characteristics.

In an embodiment, a method includes a first step involving measuring/determining sensor characteristics during the manufacturing process of the sensor. The second step involves storing these sensor characteristics into the sensor system. The third step involves a mechanism to retrieve and use these characteristics in a system that executes a closed-loop algorithm or executes a sensor signal processing algorithm (e.g. for a glucose monitoring device).

In certain example embodiments, an artificial pancreas includes an insulin delivery system (e.g.: an insulin pump, Bluetooth® enabled smart insulin pen, Bluetooth® low energy enabled smart insulin pen), a glucose sensor, and a closed-loop algorithm which generates insulin delivery commands to the pump based, in part, on inputs from the glucose sensor. The artificial pancreas includes hardware and software which work in conjunction with other analytes as well, and are not limited to glucose.

In embodiments the system further includes mechanisms needed for the components to communicate. The technical advancements and commercial adoption of smartphones and cloud-based computing has facilitated the development of artificial pancreas-type systems and methods, for example, by promoting standardized communication technologies such as Bluetooth® and the world-wide-web. An environment for realizing artificial pancreas systems that utilize these and other technologies is described below. While devices described herein are described with respect to glucose as an example of an analyte, in implementations the hardware and software described below may be used in conjunction with other analytes.

DETAILED DESCRIPTION

Architecture Considerations

Figure 1:
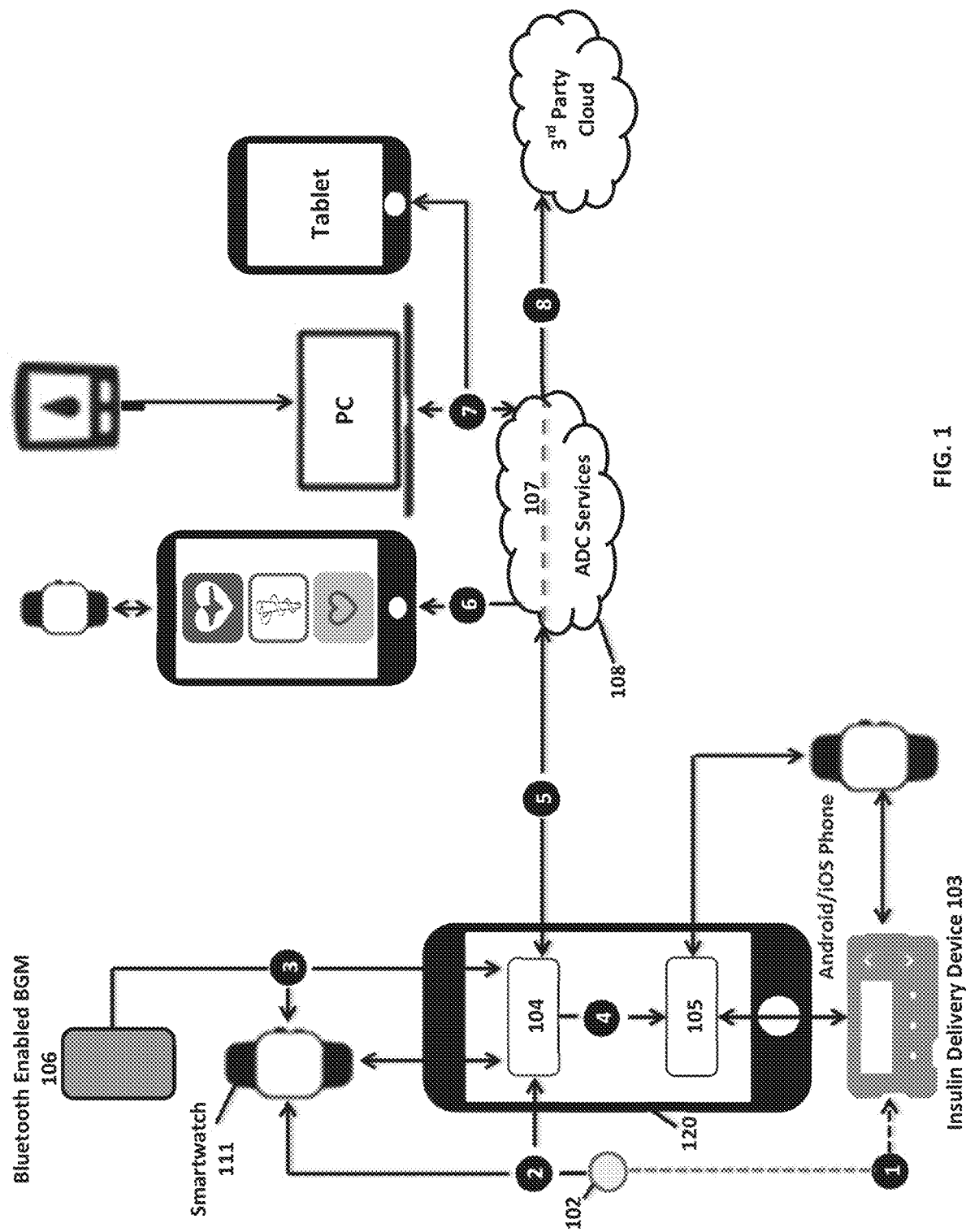
FIG. 1 illustrates a glucose monitoring system in accordance with an embodiment.

FIG. 1 illustrates a glucose monitoring system in accordance with an embodiment. Under the embodiment of FIG. 1, a glucose sensor is in communication with an intermediary device (e.g., smartphone operating a software application) which operates to control an insulin delivery device (e.g., insulin delivery device, such as an insulin pump 103).

In the embodiment of FIG. 1, sensor device 102 includes a processor and a memory storing executable instructions for a glucose calculation algorithm. Pump 103 includes a processor and memory storing executable instructions for a closed-loop insulin delivery algorithm.

In the illustration of FIG. 1, the embodiment's glucose sensor control device (SCD) 102 includes components including a housing, a sensor for in vivo placement that extends from the housing, processor and other electronics for controlling the sensor and collecting glucose measurement results, a power supply, and communication circuitry for communicating with other devices. SCD 102 can communicate directly with the insulin pump 103 over numerous kinds of communication networks. For example, in the illustration of FIG. 1, SCD 102 is in communication with insulin pump 103 via Bluetooth®. As used herein, the term "Bluetooth®" includes all varieties of Bluetooth® including standard (classic) Bluetooth® or Bluetooth® Low Energy (also called Bluetooth® SMART, Bluetooth® SMART READY, BTLE, BLE) communication (1); in this embodiment of FIG. 1, the glucose calculation algorithm is located on the sensor device 102 and the closed-loop glucose level, insulin delivery algorithm is located at the pump 103. SCD 102 also communicates via Bluetooth® to other intermediate devices (2), such as a reader device 120 (shown here to be a smartphone but could also be a dedicated use device) or a smartwatch 111, to provide user display of glucose data and to allow user input into and control of the sensor/system.

In an embodiment as in FIG. 1, the intermediate devices may also communicate via Bluetooth® to the insulin pump 103, for display of glucose data and to allow user input into and control of the system. Other devices can communicate to the intermediate devices via Bluetooth® such as a Bluetooth® enabled self-monitoring blood glucose meter (SMBG meter) 106 that can provide redundant glucose measurements for use in the closed-loop system. Finally, the intermediate devices can also communicate over the Internet (5) with a cloud-based server 108 to provide data archiving, report generation and data backup.

As mentioned, SCD 102 may communicate with a number of intermediate devices, either in an alternative fashion or simultaneously in addition. The number and types of intermediate devices may depend on, among other aspects, how much power each of these devices demands based on any constraints placed upon the underlying Bluetooth® protocol. SCD 102, which may have the tightest power constraint in the system, can provision its available battery power in order to meet the demands of multiple wireless connections with the least impact to those devices with which it communicates.

In implementations, SCD 102 accomplishes this provisioning by, among other possibilities, making concessions on one or more Bluetooth® parameters, such as communication interval, advertising interval, or transmission power. SCD 102 may also adjust its measurement cycle to achieve optimal system performance. For example, if SCD 102 were to be connected to a pump in addition to a phone, it could increase the connection interval to the phone to make up for the additional communication events needed for the pump. SCD 102 could follow a default algorithm for this kind of provisioning, with adjustment options made available to an intermediate device, such as smartphone.

Among other advantages, Bluetooth® has become a commercial standard and has incorporated low energy features that make it suitable for use with a low power consumption sensor device. However, in implementations other suitable communication technologies can be utilized instead of or in addition to Bluetooth®.

In embodiments, a physical communication connection interface can be included with the SCD 102. For example, a wired USB interface may be provided with SCD 102 for communication between SCD 102 and the insulin pump 103, to ensure communication reliability.

In an alternative embodiment, the closed-loop algorithm is stored on an intermediate device. For instance, the closed-loop algorithm may be stored in a memory of the smartphone 120 or the smartwatch 111. In such an embodiment, the SCD 102 communicates directly with the intermediate device, which in turn provides insulin delivery commands to the pump 103. An advantage of this embodiment is the potential modular approach where any closed-loop algorithm smartphone App 104 could be easily integrated with a Bluetooth® enabled sensor device and a Bluetooth® enabled insulin pump. For example, smartwatch 111 is likely worn continuously, and an embodiment where the closed-loop algorithm is located in the smartwatch 111 may thus provide advantages.

In embodiments, app 104 can exchange data with authorized 3rd party apps 105 running on the same smartphone device 120 through an app-to-app data exchange (e.g., using native operating system (OS) frameworks like, e.g., HealthKit).

In another embodiment the closed-loop algorithm is stored in the cloud 108. SCD 102 communicates the glucose data to one or more computing devices which are part of cloud 108 via the intermediate device, and the computing devices communicate the resulting insulin command to the pump via the intermediate device (e.g., 120, 111). Alternatively or in addition, SCD 102 and insulin pump 103 communicate directly via the internet to the cloud 108. One or more computing devices, SCD 102 and/or insulin pump 103 include features to compensate for internet latency and ensure reliability.

In embodiments, the communication between an SCD 102 and an on-body insulin pump 103 may occasionally be interrupted. In recognition, in an embodiment of the system, multiple communication paths are provided for data from SCD 102 to reach the insulin pump 103. For instance, the system may have multiple communication paths, e.g., a communication path to transmit glucose data directly from SCD 102 to the pump 103, and another path from SCD 102 to the pump 103 via a smartphone 120, and yet another path via a smartwatch 111. The closed-loop algorithm on the pump 103 would accept data from any of these multiple paths and could also check the data from each path to confirm that they are consistent. These redundant communication paths could also communicate other inputs intended for the closed-loop algorithm. Alternatively, the closed-loop algorithm could be redundantly stored on each of the smartphone 120, smartwatch 111, SCD 102, etc., so that the closed-loop insulin delivery instructions could be redundantly and independently transmitted to the insulin pump 103.

Another alternative embodiment is for SCD 102 to also act as a hub for other inputs to the system. Among other advantages, SCD 102 and the pump 103 may be attached to the patient's body, whereas the intermediate devices may not always be located with the body or have relatively less reliable communication interfaces for a real-time system such as an artificial pancreas. In an embodiment where SCD 102 acts as a hub, SCD 102 is the central storage for device configuration and other important information such as alarm parameters, such as alarm thresholds, snooze, and turn-off. For instance, if one connected device snoozes an alarm, it would communicate this to SCD 102, which would in turn communicate this to the other connected devices. The connected devices would locally store and keep these parameters up to date.

Connection of the system to computing devices via a cloud also provides a means for monitoring the system for safety. For instance, a medical service may be provided that monitors the closed-loop insulin delivery commands for values that exceed some threshold (either immediate values or cumulative) and notifies personnel to contact the patient to ensure that everything is Ok.

In another embodiment, the closed-loop algorithm includes a different interface module for different types of SCDs 102. This module provides the interface between the closed-loop algorithm and a particular SCD 102. This module provides for reliable communication regardless of any difference in the communication protocol between types of SCDs 102. Furthermore, because different kinds of SCD 102 have different performance characteristics, the module could be used to "normalize" the glucose data provided by SCD 102 so that the data output from the module as an input to the closed-loop control algorithm has comparable performance compared to the output from modules for different SCDs 102.

One embodiment of this normalization module is to provide an ergodic measure of the sensor system's noise model. For example, sensor "system 1" may have a random uncertainty of ±5 mg/dL in the low end and ±10% at the high end, while sensor "system 2" may have a smaller lower end uncertainty but larger high end uncertainty. Incorporating this information can be implemented by adding an upper and lower confidence interval based on these aggregate ergodic measures. The values can be obtained from clinical study data of the appropriate sensor systems.

In yet another embodiment of this normalization module, the aggregate lag between the sensor output time series and a preferred reference glucose time series (e.g. venous blood glucose, arterial blood glucose, or capillary blood glucose) obtained from clinical study data can be used by the closed-loop algorithm. For example, closed-loop algorithms that are based on output feedback, such as the PID or the e-PID, can use this information by calculating an upper and lower sensor glucose bound for every sensor output values. Closed-loop algorithms that are model-based, such as the MPC, can incorporate the amount of lag explicitly into their state observer when calculating the optimal insulin delivery profile or any countering agent such as glucagon.

The net effect of the two embodiments described above, is a normalization module that allows the closed-loop algorithm to throttle the aggressiveness of the insulin delivery (or any countering agent). A sensor system with a relatively smaller noise or smaller lag allows for the same controller to respond more aggressively than a sensor with a relatively larger noise or larger lag as described in the two embodiments above.

Power Consumption Considerations

Embodiments recognize advantages for minimizing the power consumption of SCD 102 to be low; these advantages include minimizing the size and cost of the device. As such, in implementations methods are used for keeping the power consumption of devices in the system low, such as for connected devices to only request data when they need it.

For instance, a closed-loop controller may only request data at a low sample rate when glucose levels are stable (and receive a burst of data that includes multiple samples), but request at a higher sample rate when glucose levels are changing. The sensor device may provision system resources based on demand from connected devices.

Security Considerations

Since the artificial pancreas system controls delivery of the potentially dangerous drug (insulin), access to the system should be carefully controlled. Standard means of securing access to intermediate devices may be used such as passwords and biometric access features.

However, to prevent unauthorized access to the SCD 102 communications, an alternate communication mechanism may be designed into SCD 102 that allows pairing via Bluetooth®. An example of an alternate mechanism for commercially available Bluetooth® enabled devices is an actuatable button.

Furthermore, to reduce cost and improve reliability associated with buttons, an alternate pairing solution is to use NFC as an "out of band" communication to exchange secrets for pairing and bonding. For example, many smartphones include NFC reader capability. In implementations, NFC enabled reader 120 communicates with an NFC tag in a sensor packaging, which shares a common secret code with the SCD 102. For pairing, reader 120 is placed near the NFC tag in the packaging, and pairing then occurs automatically without requiring further user interaction.

Alternatively, in implementations where a computing device (e.g., smartphones) has a camera, a barcode on the packaging could be read using the camera, which would produce a similar effect as under NFC. These communication methods function at very close proximity and are not easily intercepted by a third party, thus improving security.

Embodiments recognize that data encryption provided by the current Bluetooth® designs can be compromised and that tools are available to decrypt the Bluetooth® data packets encrypted with standard Bluetooth® encryption methods. Consequently, a more secure approach may be implemented by using application level encryption to encrypt the data so that the data security is not compromised even if the Bluetooth® level encryption is broken, such as by using Elliptic Curve cryptography and Diffie-Hellman key exchange in the application designs on top of the Bluetooth® encryption.

Another mechanism for improving the security of the pairing with SCD 102 is for the device-to-be-paired, such as a smartphone 120 or insulin pump 103, to require the user to input a code as part of the pairing process, via the user interface. The code, such as the sensor serial number or portion of the serial number, may be preinstalled in the sensor device memory (e.g., during manufacturing). The code would also be provided to the user in the sensor device packaging, user guide, or on SCD 102 itself. As part of the "out-of-box" pairing process the user would enter this code, then the device-to-be-paired would transmit the entered code to the sensor device, and the sensor device would compare this code with the code stored in its memory. If the code matches, then SCD 102 would proceed with the pairing; if the code does not match an appropriate error message will be sent to the device-to-be-paired and the pairing process will be suspended.

After initial pairing, the device-to-be-paired can download to SCD 102 another code that is attributed to the user; this code is stored on the sensor device. The code may be specified by the user, such as a PIN (personal identification number) or code by randomly generated by the device-to-be-paired. Referring to this code as a PIN, the PIN can now be used for other devices to pair with the sensor device. When another device-to-be-paired attempts to pair with the sensor device, it sends this PIN. The sensor device compares this PIN with the PIN stored in its memory. If the code matches, then the sensor device would proceed with the pairing; if the code does not match an appropriate error message will be sent to the device-to-be-paired and the pairing process will be suspended.

Algorithm Considerations

The closed-loop algorithm primarily utilizes glucose measurement data as an input; additionally, other measurements or inputs may be utilized. Examples of such inputs include past insulin delivered, current insulin command, meal information, activity information, glucose sensor temperature, blood pressure measurement, etc. Some of these measurements may be made with sensors collocated or integrated with SCD 102 and communicated directly from SCD 102 to the algorithm.

Other measurements may be transmitted or input into the smartphone device, integrated and provided and/or transmitted to the algorithm. For instance, SCD 102 may also include a temperature sensor and an accelerometer, and readings from these sensors can be integrated with the glucose data in a communication transmission and transmitted to the algorithm. These readings can be used to predict physiological responses to treatment. Specifically, a sudden drop in sensor temperature may indicate an impending hyperglycemic event.

In addition, glucose data from multiple sources may be used in the closed-loop algorithm. For instance, the sensor device may provide the primary source of glucose data for the algorithm. However, with the connectivity provided by smartphone devices, other sources of glucose data, for instance from a Bluetooth® enabled SMBG meter, can be utilized in the algorithm. The multiple sources of glucose data can be utilized in the closed-loop control algorithm using standard control design techniques. It could also be used to estimate sensor data uncertainty, which can also be used in the control algorithm.

The glucose calculation algorithm that converts raw glucose sensor measurements to glucose values may be located on SCD 102, on an intermediate communication device, such as a smartphone 120 or a cloud server 108, or at the insulin pump 103. The output of this algorithm provides the glucose values that are used in the closed-loop algorithm. Alternatively, the system may provide glucose measurements directly into the closed-loop algorithm. The glucose sensor device (or intermediate communication device) may provide both raw glucose measurements and calculated glucose measurements in the communication transmission intended for closed-loop control. Alternatively, SCD 102 (or intermediate communication device) may provide alternatively calculated glucose results; for instance, one result utilizing lag correction in the calculation algorithm and another without lag correction.

If insulin delivery information from the pump and/or closed-loop algorithm as well as other relevant information such as meal (e.g. start of a meal, relative amount, amount of carbohydrates, amount of fat or protein, consumption of alcohol) can be made available to SCD 102, then the sensor glucose calculation can take these information into account to reconcile between actual glucose change and/or change in direction versus an artifact to be rejected/ignored/compensated for. Information regarding insulin delivery can be based on available insulin delivery information, such as recent bolus amount (i.e. how many units) and profile (e.g. square wave, normal, or extended), a detected occlusion that prevents or slows insulin delivery, or latest basal insulin infusion rate.

In some closed-loop systems, in addition to the latest insulin delivery rate command, every update may include temporary basal rate to be used should there be any interruption in the insulin pump's command in the near future. In this case, the temporary basal can also be used by the sensor glucose algorithm to obtain a better estimate of the latest glucose value as well as near future glucose values.

Some sensor systems, may utilize a hybrid closed-loop algorithm in conjunction with, or in place of, a closed-loop algorithm. For example, additional input may be provided to control the insulin pump in conjunction with the algorithm. In embodiments, sensor systems may switch between modes where the closed-loop algorithm is used, and where a hybrid closed-loop algorithm is used. In embodiments, the hybrid closed-loop algorithm may be used for calculation of insulin delivery profiles as described herein.

In embodiments, a patient's initial conditions may be used as a basis for use of a closed-loop or hybrid closed-loop algorithm. For example, a patient may be characterized via open-loop glucose dynamics, and these characterizations used as initial conditions for a closed-loop or hybrid closed-loop algorithm.

The estimate of the near future glucose values as described, in combination with recent past glucose measurement values, can also be used to provide a time estimate for other components of the system such as a connected smartwatch, pump controller, or smartphone. This time estimate may include a pre-determined or adjustable glucose level threshold. For example, let the glucose level threshold be set at 5 mg/dL (or it can be a hybrid threshold of 5 mg/dL at low glucose, and 20% at high glucose). Then, at any given time, the sensor glucose algorithm may include a time estimate in the sensor signal payload.

This time estimate corresponds to the estimated duration in the near future when sensor glucose may have changed by at least that threshold. As a result, non-critical components may be able to query or update its values at a longer time interval in order to conserve its own power.

In certain applications, such as pilot closed-loop system studies, this time estimate can also be incorporated into the hazard mitigation of the study in order to alert a remote monitoring service or the study participant when the time estimate is shorter than a pre-determined value.

Continuing with the scenario of insulin delivery information from the pump and/or closed-loop algorithm as well as other relevant information such as meal being made available to the sensor, then a time-of-day pattern comparison similar to the Ambulatory Glucose Profile (AGP), normalized by the known insulin delivery and meal information, can be done to determine whether the glucose measurement values in the past few hours are out of the range of the known variation of the same time of day from the last few days. One use of this information is to remind the patient that there may be something different about this day, such as missed meal bolus, missed a meal, change in stress levels causing additional hyperglycemia, sensor adhesive failure, or an infusion set failure.

Another input into the closed-loop algorithm is various measures of uncertainty in the glucose measurement or in the anticipated glucose measurements. Uncertainty can be used in the closed-loop algorithm to adjust how much weight the algorithm places on certain algorithm inputs vs. glycemic state determined from the model incorporated into the closed-loop control system. One measure of glucose measurement uncertainty is to utilize uncertainty estimates for the glucose readings and rate-of-change generated from the glucose calculation algorithm.

In certain embodiments, sensor systems include pre-determined specifications or requirements on uncertainty. The pre-determined specification or requirements in certain embodiments are sensor system-specific. For example, a particular sensor system type has a pre-determined specification on uncertainty having a standard deviation of 11 mg/dL across the entire operating range of the sensor. Another sensor system type may have a pre-determined uncertainty defined based on coefficient of variation, for example a 14% coefficient of variation. A third sensor system can have a pre-determined uncertainty based on standard deviation characteristics, for example, a 20 mg/dL standard deviation for readings up to 154 mg/dL, and a variance of 13% for readings above 154 mg/dL. When the closed-loop algorithm obtains a reading from the sensor system, the pre-determined uncertainty associated with the particular sensor system in certain embodiments is either implicitly or explicitly used to process sensor signals.

For example, in certain embodiments, the closed-loop algorithm may take the pre-determined uncertainty into account implicitly by adopting a pre-determined rule that reduces the aggressiveness of the closed-loop controller when the latest sensor reading is associated with a higher uncertainty. By doing so, the algorithm may cause the closed-loop controller to behave more aggressively (e.g., with regard to insulin delivery) when the latest sensor reading is associated with a lower uncertainty.

In other embodiments, the closed-loop algorithm may take the pre-determined uncertainty into account explicitly by directly linking, or otherwise providing, the uncertainty information provided by and specific to the particular sensor system to a state observer component of the closed-loop controller. For example, in a state feedback-based approach that employs a state observer, such as a Kalman Filter, the influence of the latest sensor reading is tempered by the assumed uncertainty from that sensor reading. Without this sensor system type specific uncertainty information, a state observer such as a Kalman Filter in a state feedback-based approach may need to determine the measurement uncertainty separately. This may involve making a prospective determination that does not change once the determination is completed.

In certain embodiments, the pre-determined specification of uncertainty may be the expected error of each sensor system type as a function of elapsed time since the sensor start. In embodiments, due to sensor response drift, a sensor system can have a pre-determined uncertainty, e.g. a −3%/day average drift with a 5%/day standard deviation across a population of sensors of that type. Another sensor system can have a −0.5%/day average drift with a 20%/day standard deviation. The closed-loop algorithm can either use this information implicitly or explicitly. In the absence of such information, the closed-loop system may make a prospective assumption on this sensor characteristic.

In certain embodiments, the specification of uncertainty may be described by parameters associated with a particular sensor type. These parameters may take various forms when plotted, such as lines or curves. In embodiments, the parameters may correspond to an expected mean value from a priori sensor population data, a median, a mode, or other calculations which may be used to describe the population aggregate response over time. Upper and lower bounds can be determined from interquartile range or other methods.

A central trend and bounds can be pre-determined and carried by the sensor system type in various ways. In an embodiment, the sensor system carries information regarding the equations governing how the values change over time, and the necessary parameters for them. One example is the use of an exponential system of the form NormalizedResponse(t)=a1*[exp(−a2 t)−exp(−a3 t)] to describe the change of values over time. For such a system, the knowledge of the equation, plus the values for a1, a2, and a3, are then specific for that sensor system In one embodiment, an extension is made on the ergodic noise example previously described. In this particular case, the sensor glucose algorithm may link its artifact and/or noise rejection sub module to generate a time varying uncertainty value. For example, when this sub module detects a higher than average temporary increase in noise or dropouts (aka Pressure Induced Sensor Attenuation), then the closed-loop algorithm can adjust its controller aggressiveness accordingly.

In addition, if the sensor glucose algorithm alters the effective bandwidth of its filter, an estimate of the overall sensor system lag is also updated. For example, suppose a sensor system is determined to have an aggregate lag of 6 minutes relative to its preferred reference glucose as determined from clinical study data. When the sensor glucose system is operating nominally, a value of 6 minutes is made available in the sensor glucose payload for the closed-loop algorithm to use. When the sensor glucose system detects a condition that warrants more smoothing, or when other conditions trigger the sensor glucose system to apply more smoothing, then the value is increased accordingly.

Uncertainty can also be estimated from other inputs to the system. For instance, increased sensor temperature fluctuations could be detected as in indication that the glucose measurement may be more uncertain. Also, other inputs to the system such as a meal start indicator may be used as a means to indicate greater glucose measurement uncertainty, in particular with glucose measurements that exhibit lag.

In another aspect of the algorithm, when higher uncertainty is detected, the system can respond in ways to reduce the uncertainty. For instance, in response to high uncertainty, the system can request a faster sampling rate from SCD 102. SCD 102 could provide a faster sampling rate at times of uncertainty as part of an overall power management algorithm that makes other concessions to make up for the additional power to provide more data. For example, such an algorithm could sample at slower than nominal rates at other times of stable glucose. Alternatively, the sensor algorithm can detect high uncertainty, and provide data to the closed-loop control algorithm at a faster rate. If data at a faster rate is not available because of power budget limitations, the user could be notified of the situation and even be allowed to override the limitation if desired.

In other aspects of the algorithm, when a low insulin rate is detected, the glucose calculation algorithm may use more lax data quality checks when validating glucose values for further use. Alternatively, when high rates of insulin infusion are detected, the data quality checks may become strict. For example, if the user's glucose value is fluctuating in a wide range over a period of time and the user is doing frequent insulin adjustments, algorithm calculation can switch to a different configuration to require more data points in the future to accurately calculate the current real-time glucose value. Also, if a lapse in communication with the glucose sensor occurs, when the communication is reestablished, the control algorithm may request the missing data from SCD 102, or alternatively, SCD 102 may provide the missing data. The control algorithm can use this missing data to update the model state that is used in the algorithm. Depending on the closed-loop algorithm, the duration and sample interval of the recovered sensor glucose may vary. The sensor glucose system may provide a minimum number of points required to properly recreate the continuous sensor signal in that specified duration, or it may provide data in the sample interval and duration specified by the requesting closed-loop system.

In embodiments as in FIG. 1, informatics 107 may be included to provide real-time or near real-time access to selected data, through an API, to authorized apps 105 and/or devices (e.g., MySugr, Fitbit, or caregiver reader apps). The informatics 107 enable patients, health care providers (HCPs), and caregivers to upload data from supported devices (e.g., BGM 106, reader devices 120 (dedicated, smartphone, etc.) and to produce reports and view them on demand. Furthermore informatics 107 can provide access to selected data to authorized 3rd party cloud-based services (e.g., data brokers like Validic, or EMR systems like Practice Fusion).

In another aspect of the algorithm, existing closed-loop algorithms attempt to control glucose to a fixed glucose value or a fixed range of values. This disclosure contemplates using a predetermined "normal" prandial glucose profile as a closed-loop target instead of a fixed target. For example, the typical post-prandial glucose excursion could be allowed by the algorithm, causing the correction from the algorithm to be attenuated during this time. This may avoid closed loop overshoot.

In one embodiment of this "normal" profile, the sensor glucose system provides an upper target and a lower target time series points to cover the entire 24 hours (in the sense of the AGP). The system may start with a predetermined upper and lower target time series generated by the HCP or the closed-loop study organizer. As sensor glucose data is collected, a historic profile is created, containing historic lower time series. This historic lower time series reflects recent past hypoglycemia risk. If the historic lower time series is much lower than the lower target time series, the upper target time series may need to be adjusted upwards around that time of day. This prevents the closed-loop system from attempting to follow an unreasonable upper goal, by overexerting its efforts in the most difficult periods at the expense of increased risk of hypoglycemia. Over time, as other areas (of time of day) are improved, as the closed-loop system adaptive parameters improve, and as the patient makes better use of meal announcements and other use adjustments, the historic lower time series may no longer be far below the lower target time series in most areas of time of day. This allows the upper target time series to be adjusted down. The net result increases the chance of attaining better glucose control in the long run without subjecting the patient to unnecessarily high risk of hypoglycemia.

Another aspect of the closed-loop algorithm is to perform a system status check based on comparing the predicted glucose response based on planned interventions such as insulin delivery or meal inputs, with the actual measured glucose, to detect that the intervention did not occur or was different than planned. One example is detecting occlusion in the insulin delivery apparatus when the measured glucose is less than the predicted glucose. This detection could be used in conjunction with a pump-centric occlusion detection, as a redundant check.

Figure 2:
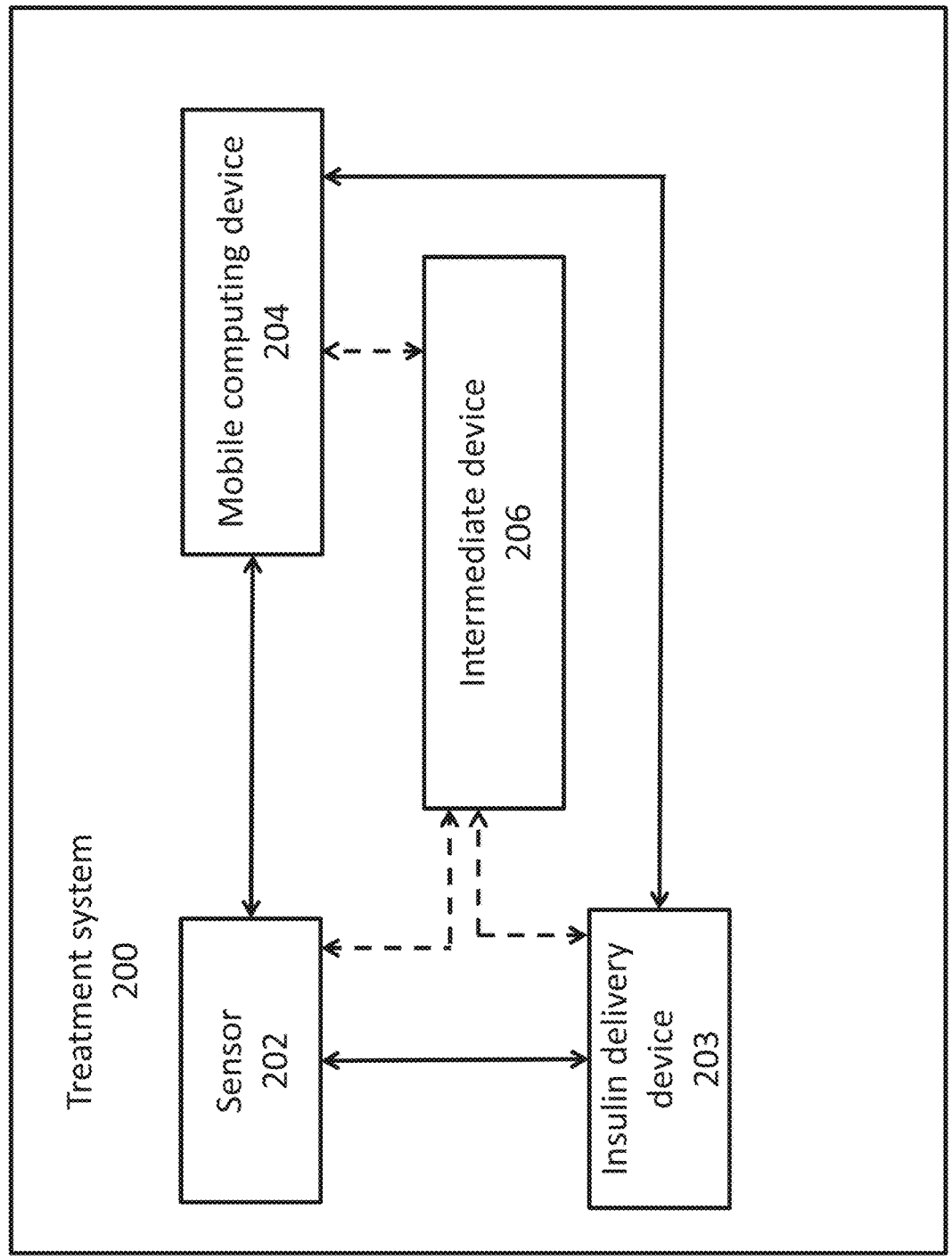
FIG. 2 illustrates a diabetes treatment system according to an embodiment.

FIG. 2 illustrates a diabetes treatment system according to an embodiment. Treatment system 200 includes a sensor 202, which includes electronics for measuring an analyte level, storing data (e.g., measurement data, sensor-related data), and transmitting and receiving data (e.g., via Bluetooth® communication). Sensor 202 is in communication with insulin delivery device 203 and a mobile computing device 204. Mobile computing device 204 includes a processor and memory to receive measurement data and/or other data from sensor 202, perform calculations, and transmit instructions to insulin delivery device 203. In embodiments, mobile computing device 204 can be a smartphone operating a software application configured to perform the previously mentioned operations. Furthermore, in the embodiment of FIG. 2, intermediate device 206 operates as an intermediary with respect to the one or more functions of mobile computing device 204 (e.g., communication, analyte calculations, error correction). In implementations, intermediate device 206 may include a processor and programming to perform one or more other operations which could otherwise be performed on mobile computing device 204 (e.g., calculations; instructions). While a single intermediate device is shown in the illustration of FIG. 2, in embodiments multiple intermediate devices may be used.

Figure 3:
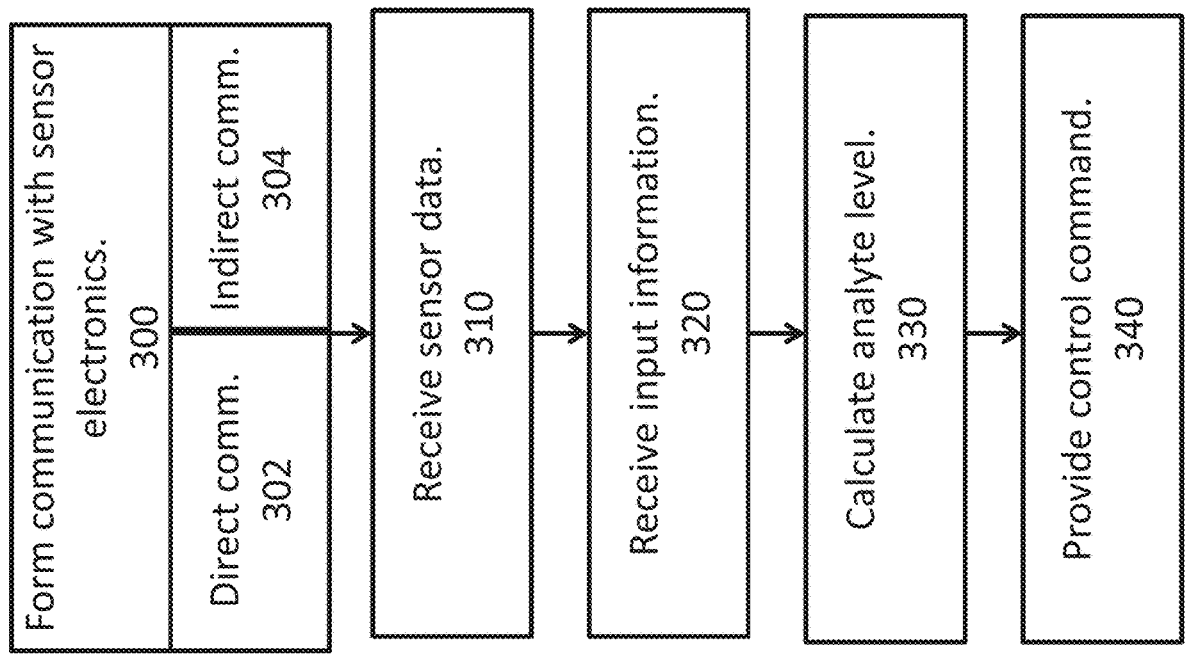
FIG. 3 illustrates a method for using a glucose monitoring system in an embodiment.

FIG. 3 illustrates a method for using a glucose monitoring system in an embodiment. A method as described in FIG. 3 may, in embodiments, be implemented with the systems described in FIGS. 1 and 2. Reference is made in describing FIG. 3 to the elements of systems of FIGS. 1 and 2.

At (300) a communication is formed with sensor electronics, either directly (302) or indirectly (304). In an embodiment, a closed-loop algorithm module (e.g., a computing device operating the closed-loop algorithm module) communicates with an on-body component of a sensor system (e.g., via a Bluetooth® Low Energy communication connection). Sensor data is received or otherwise obtained (310). For example, the device operating the closed-loop algorithm module may receive analyte level measurements from a sensor. Input information is received (320). For example, the device operating the closed-loop algorithm module may receive uncertainty data from the on-body component's memory. The data from (310) and (320) may be received from different devices; for example, the analyte level information and the input information may be received from different transmitting devices. An analyte level is calculated based, at least in part, on the received sensor data and uncertainty data (330), and a control command is provided based on the analyte level (340). For example the control command may control the amount of insulin delivered by an insulin delivery device.

In an embodiment, a closed-loop algorithm module is in direct communication with the on-body component of a sensor system (e.g. via BTLE). The measurement uncertainty information can be used to determine the aggressiveness level of the control command (e.g. how much insulin to dose at any given time). If sensor lag information is available, the closed-loop algorithm can also take that knowledge in addition to the measurement uncertainty in order to adjust the dosing decision accordingly. An example is when the closed-loop algorithm employs a form of state observer (e.g. a Kalman Filter, a Linear Quadratic Gaussian controller, or a model predictive controller), where the lag and measurement uncertainty information become parameters that are explicitly needed by the state observer calculations. Without this mechanism, every time a new sensor or sensor lot or sensor system is used, the controller parameters may need to be tuned accordingly.

In a further embodiment, a sensor signal processing algorithm is the final user of the information. Information from the on-body component can be used by the sensor signal processing algorithm to maximize the algorithm's performance. For example, when a sensor whose measurement uncertainty is relatively low is connected to the sensor signal processing algorithm module, the algorithm can adjust to perform less smoothing and increase the extent of lag correction closer to the maximum allowable setting. When the membrane lag or overall system lag is relatively small, the sensor signal processing algorithm module can decrease the extent of lag correction closer to the minimum allowable setting.

In the case of an indirect communication between a closed-loop algorithm module and the on-body component of a sensor system via a Reader, information from the on-body component can be further modified by the sensor signal processing algorithm module in the Reader. For example, the sensor signal processing algorithm can modulate the sensor information such as the measurement uncertainty in terms of a time varying variability or a time varying bias that reflects a priori in-vivo information. The sensor signal processing algorithm can also run wear-time fault detection and compensation, or any available comparison against reference BG. The Reader then communicates the information to the closed-loop algorithm module. As a result, the same closed-loop algorithm as described in the first embodiment can use the same type of information, but with the benefit of additional temporal refinement/adjustment by the sensor signal processing algorithm module in the Reader.

Figure 4:
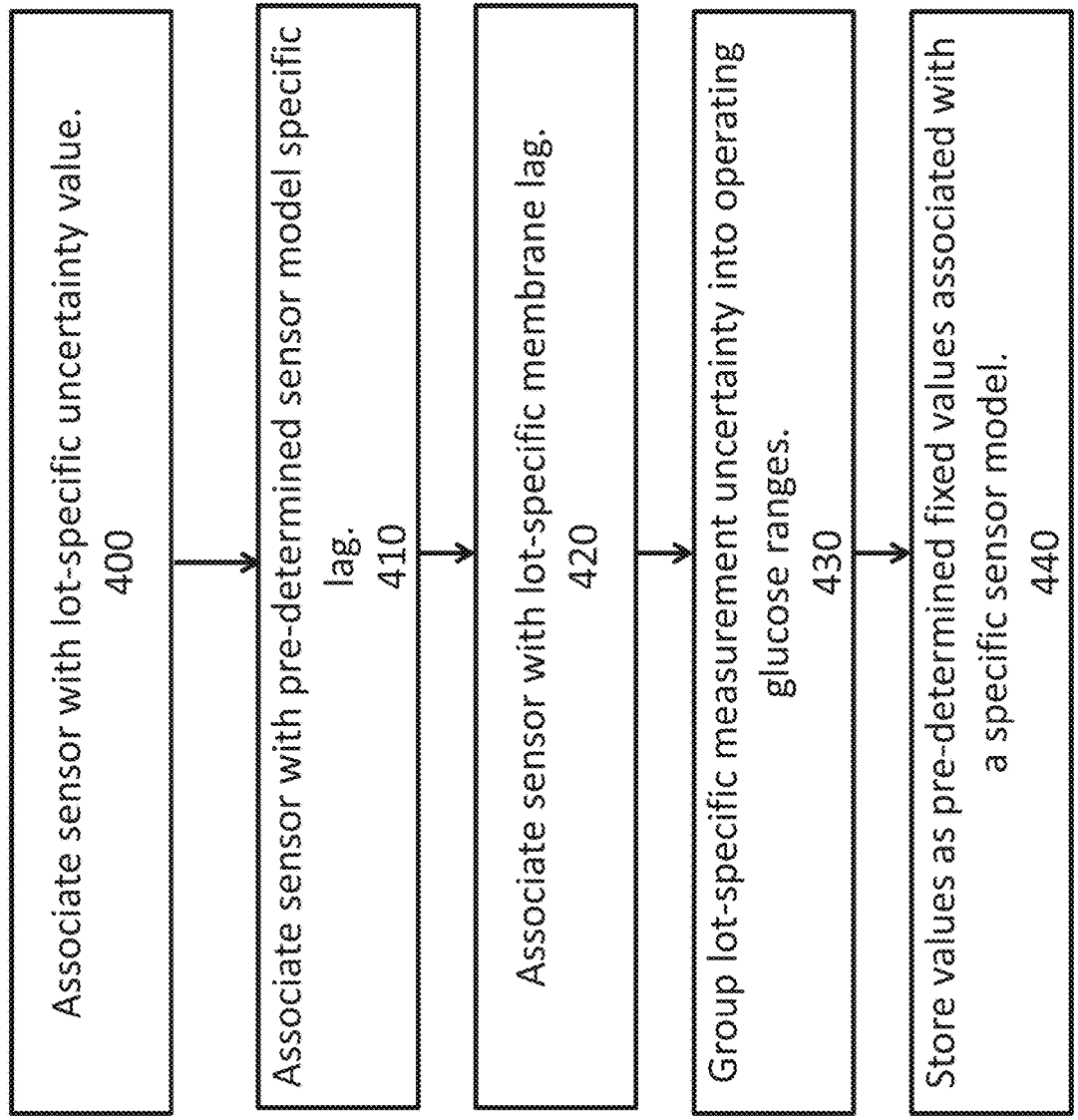
FIG. 4 illustrates a method for preparing a sensor assembly for use in a glucose monitoring system in an embodiment.

FIG. 4 illustrates a method for preparing a sensor assembly for use in a glucose monitoring system in an embodiment. A method as described in FIG. 4 may, in embodiments, be implemented with the systems described in FIGS. 1 and 2. Reference is made in describing FIG. 4 to the elements of systems of FIGS. 1 and 2.

During the manufacturing process, a sensor lot is characterized by performing a series of tests on a sample batch.

One of the information obtained from this batch sample is the sensor-to-sensor in-vitro uncertainty (e.g. in terms of coefficient of variation). In addition, the response time of each sample is measured, relative to stepwise changing concentration of glucose in the testing system. Numerous kinds of information and pre-determined characteristics (e.g., lot-specific measurement uncertainty value, pre-determined sensor model specific lag, lot-specific membrane lag) can be captured during the manufacturing process.

A sensor in a sensor lot is associated with a lot-specific measurement uncertainty value (400). In embodiments, this can be obtained by measuring the coefficient of variation (CV) of the in-vitro batch sample's signal response to glucose at various known glucose concentrations relative to the curve fitted to the data. It can also be obtained in terms of the standard deviation of the same dataset, inter-quartile range of the same dataset, or other statistical measures that reflect the measurement uncertainty.

The sensor is associated with a pre-determined sensor model specific lag (410). The sensor model specific lag can be influenced by the intended sensor insertion site and the type of reference BG used to assess system performance. For example, a transcutaneous sensor that measures interstitial glucose relative to a capillary BG reference can be assumed to have a relatively larger lag than the same transcutaneous sensor that measures the same interstitial glucose relative to a reference interstitial fluid concentration.

The sensor is associated with a lot-specific membrane lag (420). A lot-specific membrane lag can be calculated from the time response of the batch sample sensors relative to the stepwise changing known glucose concentration in the testing system.

In embodiments, the lot-specific measurement uncertainty may be grouped into several operating glucose ranges (430). For example, the use of 3 glucose ranges will then store 3 different lot-specific measurement uncertainty for the low, medium, and high glucose ranges, where the boundaries of each glucose ranges are pre-determined.

The values are stored as pre-determined fixed values associated with a specific sensor model (440). For example the measurement uncertainty and sensor lag data may be stored in a memory of the sensor.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

All software described herein, and all actions of devices can be performed or executed with processing circuitry, such as, e.g., a microprocessor, a microcontroller, an applications processor, a communications processor, a programmable gate array, or one or more of the preceding examples operating in conjunction with each other. Non-transitory memories can store a plurality of instructions that, when executed by the processing circuitry, cause the software to be performed and/or the described actions to be taken. Examples of non-transitory memory include volatile and nonvolatile memory, RAM, ROM, hard disk drives, and the like.

What is claimed is:

1. A system for managing a patient's glucose level, the system comprising:
    a glucose sensor to generate and store data signals for measurements of the patient's glucose level made by the glucose sensor;
    an insulin delivery system;
    sensor electronics operatively coupled to the glucose sensor, the sensor electronics comprising a memory storing one or more predetermined sensor characteristics associated with the sensor electronics; and
    a computing device in electronic communication with the sensor electronics, the computing device comprising a processor configured to operate the sensor electronics to (i) receive the generated data signals, (ii) obtain the one or more predetermined sensor characteristics from the memory and (iii) execute a closed-loop algorithm to provide insulin delivery instructions to an insulin delivery system by at least using the data signals and predetermined sensor characteristics;
    wherein the predetermined sensor characteristics used by the closed-loop algorithm to provide insulin delivery instructions to an insulin delivery system include at least one of a lot-specific measurement uncertainty and a lot-specific membrane lag.

2. The system of claim 1, wherein the one or more predetermined sensor characteristics further comprise sensor-specific characteristics.

3. The system of claim 1, wherein the one or more predetermined sensor characteristics are determined during lot manufacturing of the sensor electronics.

4. The system of claim 3, wherein the one or more predetermined sensor characteristics correspond to one or more sensor characteristics determined during lot manufacturing from a sample of sensors in the lot.

5. The system of claim 1, where the computing device communicates with the sensor electronics over a Bluetooth® communication link.

6. The system of claim 1, wherein the predetermined sensor characteristics further includes a sensor model-specific lag.

7. The system of claim 1, wherein the computing device communicates with the sensor electronics over the Internet.

8. The system of claim 1, wherein the processor is further configured to receive additional glucose data from numerous sources besides the glucose sensor, and to execute the closed-loop algorithm to provide insulin delivery instructions to the insulin delivery system by further using the additional glucose data.

9. The system of claim 8, wherein the processor is further configured to receive the additional glucose data over multiple communication paths, and to confirm that the additional data is consistent with the measurements from the glucose sensor.

10. The system of claim 1, wherein the electronic computing device comprises at least one of (i) a smartphone (ii) a smartwatch or (iii) a cloud-based server.

11. A system for adjusting a patient's glucose level, comprising:
- a glucose sensor comprising a sensor subsystem to measure a patient's blood glucose concentration, the sensor subsystem including a memory to store the blood glucose concentration measurements, the memory further storing one or more predetermined sensor characteristics associated with the glucose sensor; and
- a computing device comprising a processor configured to provide results to a user for the blood glucose concentration by at least retrieving the blood glucose concentration measurements from the memory of the sensor subsystem, retrieving the one or more predetermined sensor characteristics associated with the glucose sensor, and using the predetermined sensor characteristics to adjust the extent of signal smoothing and lag correction for the results to be provided;
- wherein the predetermined sensor characteristics used to adjust the extent of signal smoothing and lag correction include at least one of a lot-specific measurement uncertainty and a lot-specific membrane lag.

12. The system of claim 11, wherein the one or more predetermined sensor characteristics further comprise sensor-specific characteristics.

13. The system of claim 11, wherein the one or more predetermined sensor characteristics are determined during lot manufacturing of the glucose sensor.

14. The system of claim 13, wherein the one or more predetermined sensor characteristics correspond to one or more sensor characteristics determined during lot manufacturing from a sample of sensors in the lot.

15. The system of claim 11, where the computing device communicates with the sensor subsystem over a Bluetooth® communication link.

16. The system of claim 11, wherein the predetermined sensor characteristics further includes a sensor model-specific lag.

17. The system of claim 11, wherein the computing device communicates with the sensor subsystem over the Internet.

18. The system of claim 11, wherein the processor is further configured to receive additional glucose data from numerous sources besides the glucose sensor, and to execute a closed-loop algorithm to provide insulin delivery instructions to an insulin delivery system by further using the additional glucose data.

19. The system of claim 18, wherein the processor is further configured to receive the additional glucose data over multiple communication paths, and to confirm that the additional data is consistent with the measurements from the sensor subsystem.

20. The system of claim 11, wherein the computing device comprises at least one of (i) a smartphone (ii) a smartwatch or (iii) a cloud-based server.

21. The system of claim 1, wherein the insulin delivery system includes an insulin pump.

22. The system of claim 1, wherein the insulin delivery system includes an insulin pen.

23. The system of claim 18, wherein the insulin delivery system includes an insulin pump.

24. The system of claim 18, wherein the insulin delivery system includes an insulin pen.

* * * * *